United States Patent
Zeng et al.

(10) Patent No.: US 11,944,957 B2
(45) Date of Patent: Apr. 2, 2024

(54) GLASS FIBER FILTER ELEMENT FOR VISIBLE LIGHT PHOTOCATALYSIS AND AIR PURIFICATION AND PREPARATION METHOD THEREOF

(71) Applicants: Chongqing Institute of East China Normal University, Chongqing (CN); ROI Optoelectronics Technology CO, LTD., Shanghai (CN); East China Normal University, Shanghai (CN)

(72) Inventors: Heping Zeng, Chongqing (CN); Mengyun Hu, Chongqing (CN); Guang Feng, Chongqing (CN)

(73) Assignees: CHONGQING INSTITUTE OF EAST CHINA NORMAL UNIVERSITY, Chongqing (CN); ROI OPTOELECTRONICS TECHNOLOGY CO, LTD., Shanghai (CN); EAST CHINA NORMAL UNIVERSITY, Shanghai (CN)

( * ) Notice: Subject to any disclaimer, the term of this patent is extended or adjusted under 35 U.S.C. 154(b) by 247 days.

(21) Appl. No.: 17/529,014

(22) Filed: Nov. 17, 2021

(65) Prior Publication Data
US 2022/0152592 A1 May 19, 2022

(30) Foreign Application Priority Data
Nov. 17, 2020 (CN) .......................... 202011283198.0

(51) Int. Cl.
*B01J 23/50* (2006.01)
*A61L 9/18* (2006.01)
(Continued)

(52) U.S. Cl.
CPC ................. *B01J 23/50* (2013.01); *A61L 9/18* (2013.01); *B01D 39/2024* (2013.01);
(Continued)

(58) Field of Classification Search
CPC ... B01J 23/50; B01J 21/18; B01J 23/04; B01J 23/06; B01J 35/0013; B01J 35/004;
(Continued)

(56) References Cited

U.S. PATENT DOCUMENTS

2016/0194474 A1 * 7/2016 Hasegawa ................ C09C 1/46
524/584

FOREIGN PATENT DOCUMENTS

| CN | 103288416 A | * | 9/2013 | ............. C04B 30/02 |
| CN | 107469648 A | * | 12/2017 | ......... B01D 67/0002 |

(Continued)

OTHER PUBLICATIONS

CNIPA, First Office Action for CN Application No. 202011283198.0, dated May 12, 2022.
(Continued)

*Primary Examiner* — Patricia L. Hailey
(74) *Attorney, Agent, or Firm* — Hodgson Russ LLP

(57) ABSTRACT

A glass fiber filter element for visible light photocatalysis and air purification and a method for preparing the same. The glass fiber filter element includes 4 to 7 wt % of nanoparticles including at least one selected from zinc oxide, graphene oxide, titanium oxide, and reduced graphene oxide, 2 to 7 wt % of silver nanowires, 3 to 12 wt % of an adhesive system, and 78 to 91 wt % of a glass fiber mat, based on the total weight of the glass fiber filter element. The glass fiber mat is made of at least two glass fibers with different diameters, and the diameters are in a range of 0.15 to 3.5 μm. The nanoparticles have a particle size from 1 to 200 nm, and the silver nanowires have a diameter of 15 to 50 nm.

19 Claims, 2 Drawing Sheets

(51) Int. Cl.
| | |
|---|---|
| *B01D 39/20* | (2006.01) |
| *B01D 46/00* | (2022.01) |
| *B01D 53/88* | (2006.01) |
| *B01J 21/18* | (2006.01) |
| *B01J 23/04* | (2006.01) |
| *B01J 23/06* | (2006.01) |
| *B01J 35/23* | (2024.01) |
| *B01J 35/39* | (2024.01) |
| *B01J 35/58* | (2024.01) |
| *B01J 37/02* | (2006.01) |
| *B01J 37/10* | (2006.01) |
| *C03C 25/1095* | (2018.01) |
| *C03C 25/16* | (2006.01) |
| *C03C 25/46* | (2006.01) |
| *C03C 25/47* | (2018.01) |

(52) U.S. Cl.
CPC ..... *B01D 46/0001* (2013.01); *B01D 46/0028* (2013.01); *B01D 53/885* (2013.01); *B01J 21/18* (2013.01); *B01J 23/04* (2013.01); *B01J 23/06* (2013.01); *B01J 35/23* (2024.01); *B01J 35/39* (2024.01); *B01J 35/58* (2024.01); *B01J 37/0219* (2013.01); *B01J 37/0236* (2013.01); *B01J 37/10* (2013.01); *C03C 25/1095* (2013.01); *C03C 25/16* (2013.01); *C03C 25/46* (2013.01); *C03C 25/47* (2018.01); *A61L 2209/14* (2013.01); *B01D 2239/0258* (2013.01); *B01D 2239/0407* (2013.01); *B01D 2239/0442* (2013.01); *B01D 2239/0618* (2013.01); *B01D 2239/0636* (2013.01); *B01D 2239/064* (2013.01); *B01D 2239/10* (2013.01); *B01D 2255/104* (2013.01); *B01D 2255/20707* (2013.01); *B01D 2255/20792* (2013.01); *B01D 2255/802* (2013.01); *B01D 2257/708* (2013.01); *B01D 2279/65* (2013.01)

(58) Field of Classification Search
CPC .. B01J 35/06; B01J 37/03219; B01J 37/0236; B01J 37/10; C03C 25/47; C03C 25/1095; C03C 25/16; C03C 25/46; A61L 9/18; A61L 2209/14; B01D 2239/0258; B01D 2239/0407; B01D 39/2024; B01D 46/0001; B01D 46/0028; B01D 53/885; B01D 2239/064; B01D 2239/10; B01D 2255/104; B01D 2255/20707; B01D 2255/20792; B01D 2255/802; B01D 2257/708; B01D 2279/65
USPC ........................................ 502/183, 343, 350
See application file for complete search history.

(56) References Cited

FOREIGN PATENT DOCUMENTS

| | | | | |
|---|---|---|---|---|
| CN | 107469648 A | | 12/2017 | |
| CN | 107825810 A | * | 3/2018 | ............ B32B 37/00 |
| CN | 109304060 A | * | 2/2019 | ............ B01D 39/20 |
| CN | 109304060 A | | 2/2019 | |
| CN | 111892330 A | * | 11/2020 | ............ B01D 53/74 |
| CN | 111892330 A | | 11/2020 | |
| KR | 20160047636 A | * | 5/2016 | ............ B23B 17/10 |
| WO | WO-2012127915 A1 | * | 9/2012 | ............ C03C 17/007 |
| WO | WO-2014102603 A1 | * | 7/2014 | ............ C08J 5/005 |

OTHER PUBLICATIONS

CNIPA, Second Office Action for CN Application No. 202011283198.0, dated Aug. 4, 2022.

* cited by examiner

GLASS FIBER FILTER ELEMENT FOR VISIBLE LIGHT PHOTOCATALYSIS AND AIR PURIFICATION AND PREPARATION METHOD THEREOF

CROSS-REFERENCE TO RELATED APPLICATION

This application claims priority to, and the benefits of, Chinese Patent Application Serial No. 202011283198.0, filed on Nov. 17, 2020, the entire content of which is incorporated herein by reference.

FIELD

The present disclosure relates to a technical field of composite functional materials, and specifically relates to a glass fiber filter element for visible light photocatalysis and air purification and a preparation method thereof.

BACKGROUND

Air quality is closely related to human health. In a relatively closed room with a high population density, microorganisms are easily spread in the air through droplets, and odors produced by human sweat gland, food, fragrance are unpleasantly strong, which will affect environmental comfort. Air purifiers are widely used to improve the air quality to meet the requirements for the living environment. For an air purifier, an air filter element is used to capture suspended particles in the air through a network structure interlacing glass fibers or polymer fibers together. Therefore, device makers need to increase the capacity and efficiency of the air filter element to improve the performance of the air purifier.

SUMMARY

Accordingly, the present disclosure provides in embodiments a glass fiber filter element for visible light photocatalysis and air purification and a method for preparing a glass fiber filter element for visible light photocatalysis and air purification.

In a first aspect of the present disclosure, a glass fiber filter element for visible light photocatalysis and air purification is provided. The glass fiber filter element includes 4 to 7 wt % of nanoparticles including at least one selected from zinc oxide, graphene oxide, titanium oxide, and reduced graphene oxide, 2 to 7 wt % of silver nanowires, 3 to 12 wt % of an adhesive system, and 78 to 91 wt % of a glass fiber mat, based on the total weight of the glass fiber filter element. The glass fiber mat is made of at least two glass fibers with different diameters, and the diameters are in a range of 0.15 to 3.5 μm. The nanoparticles have a particle size from 1 to 200 nm, and the silver nanowires have a diameter of 15 to 50 nm.

In some embodiments, the glass fiber mat includes: 2.5 to 7.5 wt % of $Al_2O_3$, 4.5 to 8.5 wt % of MgO, 1.5 to 4.5 wt % of CaO, 3 to 6.5 wt % of $B_2O_3$, 4.5 to 7.5 wt % of a mixture of $Fe_2O$, ZnO and BaO, 8 to 10.5 wt % of an alkali metal oxide $R_2O$ where $R_2O$ is selected from $Na_2O$, $K_2O$ and a combination thereof, 56.5 to 66.5 wt % of $SiO_2$, based on the total weight of the glass fiber mat.

In some embodiments, the glass fiber mat is a matrix, and the nanoparticles and the silver nanowires are introduced by formation of a seed layer and in-situ growth.

In some embodiments, the glass fiber mat has a three-dimensional network porous structure, and the glass fibers with different diameters are mutually interlaced.

In some embodiments, the adhesive system includes an adhesive and a modifier.

In some embodiments, the adhesive is at least one selected from a pure acrylic emulsion, a silicone acrylic emulsion, a styrene acrylic emulsion, a vinegar acrylic emulsion and a modified phenolic resin. An amount of the adhesive is in a range of 2 to 5 wt % of the total weight of the glass fiber filter element.

In some embodiments, the modified phenolic resin is selected from a urea-modified phenolic resin, a polyurethane-modified phenolic resin and a melamine-modified phenolic resin.

In some embodiments, the modifier is at least one selected from silane coupling agents KH550, KH560, and KH792, and an amount of the modifier is in a range of 1 to 3 wt % of the total weight of the glass fiber filter element.

In some embodiments, a zinc source for providing zinc oxide of the nanoparticles is at least one selected from zinc nitrate hexahydrate, zinc acetate, zinc sulfate, and zinc carbonate.

In some embodiments, a titanium source for providing titanium oxide of the nanoparticles is at least one selected from tetrabutyl titanate, titanium tetrachloride, and titanium alkoxide.

In some embodiments, the nanoparticles have a particle size from 1 to 10 nm.

In a second aspect of the present disclosure, a method for preparing a glass fiber filter element for visible light photocatalysis and air purification is provided. The method includes: (1) selecting two or more glass fiber mats with different glass fiber diameters, putting the glass fiber mats into a mixed liquid containing nanoparticles and silver nanowires, and using a fiber dissociator for stirring the mixed liquid to obtain a slurry; (2) transporting the slurry to a paper machine for wet forming to obtain a wet paper with a seed layer of the nanoparticles, immersing the wet paper in an adhesive system, and drying the wet paper to obtain a glass fiber paper; (3) immersing the glass fiber paper in a solution including the nanoparticles or precursors thereof, and drying the glass fiber paper; (4) performing an annealing process on the glass fiber paper to obtain a filter paper; and (5) folding the filter paper in a zigzag shape to obtain the glass fiber filter element.

In some embodiments, the glass fiber mat has glass fibers with a diameter of 0.15 to 3.5 μm.

In some embodiments, two glass fiber mats are used, and one of the glass fiber mats has a glass fiber diameter of 3.0 μm and the other one of the glass fiber mats has a glass fiber diameter of 1.0 μm.

In some embodiments, in step (1), the fiber dissociator has a revolving speed of 5000 to 12000 rpm, and the slurry has a concentration of 5 to 10 wt % and a pH value of 3.0 to 5.0.

In some embodiments, the drying in step (2) is baking on a drying plate at a temperature of 100 to 115° C. for 5±1 min.

In some embodiments, the solution in step (3) includes a zinc oxide precursor solution, and the zinc oxide precursor solution is prepared by dissolving zinc acetate in deionized water, adding ammonia to obtain a precipitate, filtering the precipitate and drying the precipitate, and preparing the zinc oxide precursor solution having a molar concentration of 0.5 to 3.0 mol/L with the precipitate, ammonia and deionized water.

In some embodiments, the solution in step (3) includes a graphene oxide solution, and the graphene oxide solution is prepared by dissolving glucose in deionized water to obtain an aqueous solution, heating the aqueous solution in a water bath at a temperature of 40 to 60° C. for 6 to 8 h, putting the aqueous solution in a Teflon reaction kettle, and placing the reaction kettle in a constant temperature blast drying oven at a temperature of 160 to 200° C. for 10 to 12 h, followed by standing for settlement and taking a supernatant as the graphene oxide solution.

In some embodiments, during the immersing in the step (2), the wet paper is lifted up at a lifting speed in a range of 0.5 to 5 cm/min.

In some embodiments, the annealing process in the step (4) is performed in an $H_2$ atmosphere at a temperature of 100° C. to 400° C. for 1 to 4 h.

DETAILED DESCRIPTION

Figure 1:
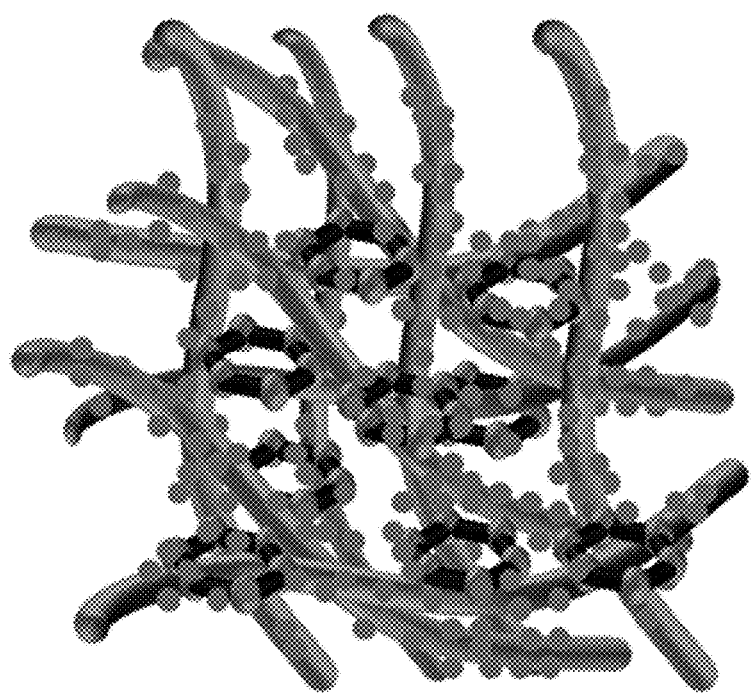
FIG. 1 is a schematic diagram of a structure of a glass fiber filter element according to an embodiment of the present disclosure.

Embodiments of the present disclosure are described in detail below, examples of which are illustrated in the drawings. The same or similar elements are denoted by same reference numerals in different drawings unless indicated otherwise. The embodiments described herein with reference to drawings are explanatory, and used to generally understand the present disclosure. The embodiments shall not be construed to limit the present disclosure.

In a first aspect of the present disclosure, the glass fiber filter element for visible light photocatalysis and air purification is provided.

In some embodiments, the glass fiber filter element includes 4 to 7 wt % of nanoparticles, 2 to 7 wt % of silver nanowires, 3 to 12 wt % of an adhesive system, and 78 to 91 wt % of a glass fiber mat, based on the total weight of the glass fiber filter element.

The glass fiber mat used in the present disclosure may be made of at least two kinds of glass fibers with different fiber diameters in a range of 0.15 to 3.5 μm. The glass fiber mat includes 2.5 to 7.5 wt % of $Al_2O_3$, 4.5 to 8.5 wt % of MgO, 1.5 to 4.5 wt % of CaO, 3 to 6.5 wt % of $B_2O_3$, 4.5 to 7.5 wt % of a mixture of $Fe_2O$, ZnO and BaO, 8 to 10.5 wt % of an alkali metal oxide $R_2O$ where $R_2O$ is selected from $Na_2O$, $K_2O$ and a combination thereof, 56.5 to 66.5 wt % of $SiO_2$, based on the total weight of the glass fiber mat. The superfine fibers with different diameters used in the present disclosure are mutually interlaced and thus construct a three-dimensional network porous structure which is stable and has a good mechanical property.

The glass fiber mat is used as a matrix, and the nanoparticles and the silver nanowires are introduced by formation of a seed layer and in-situ growth. The nanoparticles and the silver nanowires are mixed and distributed on a surface of the glass fiber mat, and the glass fiber mat maintains the three-dimensional network porous structure and has a good air filtration performance.

The nanoparticles include at least one selected from zinc oxide, graphene oxide, titanium oxide, and reduced graphene oxide, and have a diameter from 1 to 200 nm. The nanoparticles can be prepared by a microwave synthesis method, a precipitation method, a sol-gel method, or a hydrothermal method. The nanoparticles are introduced into the glass fiber filter element by in-situ growth. After the nanoparticles are densely and uniformly distributed on the glass fibers, the glass fiber filter element still has the three-dimensional porous structure, and has a good air filtration performance.

An example for the nanoparticles are zinc oxide nanoparticles. A zinc source for providing the zinc oxide nanoparticles is at least one selected from zinc nitrate hexahydrate, zinc acetate, zinc sulfate, and zinc carbonate. In another example, the nanoparticles are titanium oxide nanoparticles. A titanium source for providing the titanium oxide nanoparticles is at least one selected from tetrabutyl titanate, titanium tetrachloride, and titanium alkoxide.

The silver nanowires have a diameter of 15 to 50 nm. The silver nanowires are prepared by a template method, a polyol method, a hydrothermal method, or a wet chemical method. The silver nanowires are introduced into the glass fiber filter element by in-situ growth.

By loading the nanoparticles and the silver nanowires on the glass fibers in the present disclosure, the glass fiber air filter element of the present application has a good sterilization effect, which can effectively inhibit the growth of microorganisms on the filter element, and can also effectively degrade odor molecules and volatile organic compounds (such as benzene, toluene, ammonia, etc.) in the air under a visible light condition. The air filter element of the present disclosure does not need to add an additional layer or layers of adsorbent materials or catalytic materials, and thus reduces its own weight and volume while achieving a good air purification effect. Compared with devices that need to use UV-light to degrade the harmful gas in the air, the filter element of the present disclosure has a wider applicability.

The adhesive system used in the present disclosure may be in an amount of 3 to 8 wt % of an adhesive system based on the total weight of the glass fiber filter element. The adhesive system includes an adhesive and a modifier. The adhesive is at least one selected from a pure acrylic emulsion, a silicone acrylic emulsion, a styrene acrylic emulsion, a vinegar acrylic emulsion and a modified phenolic resin such as a urea-modified phenolic resin, a polyurethane-modified phenolic resin and a melamine-modified phenolic resin. An amount of the adhesive is in a range of 2 to 5 wt % of the total weight of the glass fiber filter element. The modifier is at least one selected from silane coupling agents KH550, KH560, and KH792, and an amount of the modifier is in a range of 1 to 3 wt % of the total weight of the glass fiber filter element. The adhesive system can improve a binding force between the nano-scale materials and the glass fibers.

In a second aspect of the present disclosure, a method for preparing a glass fiber filter element for visible light photocatalysis and air purification is provided.

In some embodiments, the method includes: (1) selecting two or more glass fiber mats with different glass fiber diameters, putting the glass fiber mats into a mixed liquid containing nanoparticles and silver nanowires, and using a fiber dissociator for stirring the mixed liquid to obtain a slurry; (2) transporting the slurry to a paper machine for wet forming to obtain a wet paper with a seed layer of the nanoparticles, immersing the wet paper in an adhesive system, and drying the wet paper to obtain a glass fiber paper; (3) immersing the glass fiber paper in a solution including the nanoparticles or precursors thereof, and drying the glass fiber paper; (4) performing an annealing process on the glass fiber paper to obtain a filter paper; and (5) folding the filter paper in a zigzag shape to obtain the glass fiber filter element.

It should be noted that all features and advantages of the materials and processes of the filter element described in the embodiments of the first aspect are also applicable to the preparation method thereof.

As described above, the two or more glass fiber mats have different fiber diameters, and all the diameters are within the range of 0.15 to 3.5 μm. For example, two glass fiber mats, a glass fiber mat with a fiber diameter of 3.0 μm and another glass fiber mat with a fiber diameter of 1.0 μm are used.

The slurry in step (1) may be stirred at a revolving speed of 5000 to 12000 rpm. The slurry has a concentration of 5 to 10 wt % and a pH value of 3.0 to 5.0. After the materials in the slurry are mixed uniformly, they are formed into a paper by the paper machine. The formed paper includes the glass fiber mat as a matrix and the nanoparticles and Ag nanowires distributed on the matrix as a seed layer. To improve the bonding force between the nano-scale materials and the glass fibers, the formed paper is immersed in the adhesive system which may be a dilute solution of the adhesive and the modifier. The paper immersed is lifted up, for example at a speed of 0.5 to 5 cm/min, and is subjected to drying as shown in step (2).

The drying in step (2) may refer to baking the paper on a drying plate at a temperature of 100 to 115° C. for 5±1 min. The obtained paper is further immersed in a solution including the nanoparticles or precursors thereof, and is dried as described in step (3). This immersing and drying process can be repeated for multiple times.

As described above, the nanoparticles may be selected from the group consisting of zinc oxide, graphene oxide, titanium oxide, and reduced graphene oxide. The nanoparticles in steps (1) and (3) may be the same or different. For example, the nanoparticles in step (1) are zinc oxide alone or zinc oxide and graphene oxide. The solution in step (3) may include a zinc oxide precursor and reduced graphene oxide.

Further, the solution in step (3) may include zinc oxide precursor solution. The zinc oxide precursor solution is prepared by dissolving zinc acetate in deionized water, adding ammonia to obtain a precipitate, filtering the precipitate and drying the precipitate, and preparing the zinc oxide precursor solution having a molar concentration of 0.5 to 3.0 mol/L with the precipitate, ammonia and deionized water.

Further, the solution in step (3) may include a graphene oxide solution. The graphene oxide solution is prepared by dissolving glucose in deionized water to obtain an aqueous solution, heating the aqueous solution in a water bath at a temperature of 40 to 60° C. for 6 to 8 h, putting the aqueous solution in a Teflon reaction kettle, and placing the reaction kettle in a constant temperature blast drying oven at a temperature of 160 to 200° C. for 10 to 12 h, followed by standing for settlement and taking a supernatant as the graphene oxide solution. A carbon precursor may be used for preparing the graphene oxide solution, and is selected from the group consisting of starch, biomass, bamboo, carbon black, and graphite. In process, the carbon precursor is subjected to hydrothermal treatment to produce at least one selected from graphene, graphene oxide, reduced graphene oxide, and graphene quantum dots.

After the paper is immersed with the nanoparticle solution in the step (3) for 3 to 10 min, the wet paper is lifted up at a lifting speed in a range of 0.5 to 5 cm/min, followed by drying at 100 to 150° C. for 3 to 10 min.

The annealing process in the step (4) refers to a process of subjecting the dried paper obtained in the step (3) in an $H_2$ atmosphere at a temperature of 100° C. to 400° C. for 1 to 4 h. The annealing process is used to allow the nanoparticles and the nanowires to grow in situ.

Further, in the step (1), at least one selected from graphene, graphene oxide, reduced graphene oxide, and graphene quantum dots is attached to surfaces of the glass fibers with different diameters, which increases attachment sites for the nanoparticles, facilitates the production of relatively small nanoparticles such as zinc oxide, allowing the nanoparticles to uniformly distributed, thus reducing agglomeration. In this case, for example, zinc acetate is dissolved in deionized water, ammonia is added to obtain a precipitate of zinc oxide having a particle size of 1 to 10 nm, and the glass fibers are immersed to allow zinc oxide to grow on a surface of the at least one selected from graphene, graphene oxide, reduced graphene oxide, and graphene quantum dots.

In the present disclosure, the nanoparticles are served as a photocatalytic catalyst based on graphene, graphene oxide, reduced graphene oxide, graphene quantum dots or any combination thereof, which is surface-modified with titanium dioxide, zinc oxide or their combination. With the nanoparticles, a visible light response and an adsorption characteristic can be adjusted. With the loading of the nano-scale materials (i.e., the nanoparticles and the nanowires), the specific surface area of the glass fiber filter element can be increased.

Figure 2:
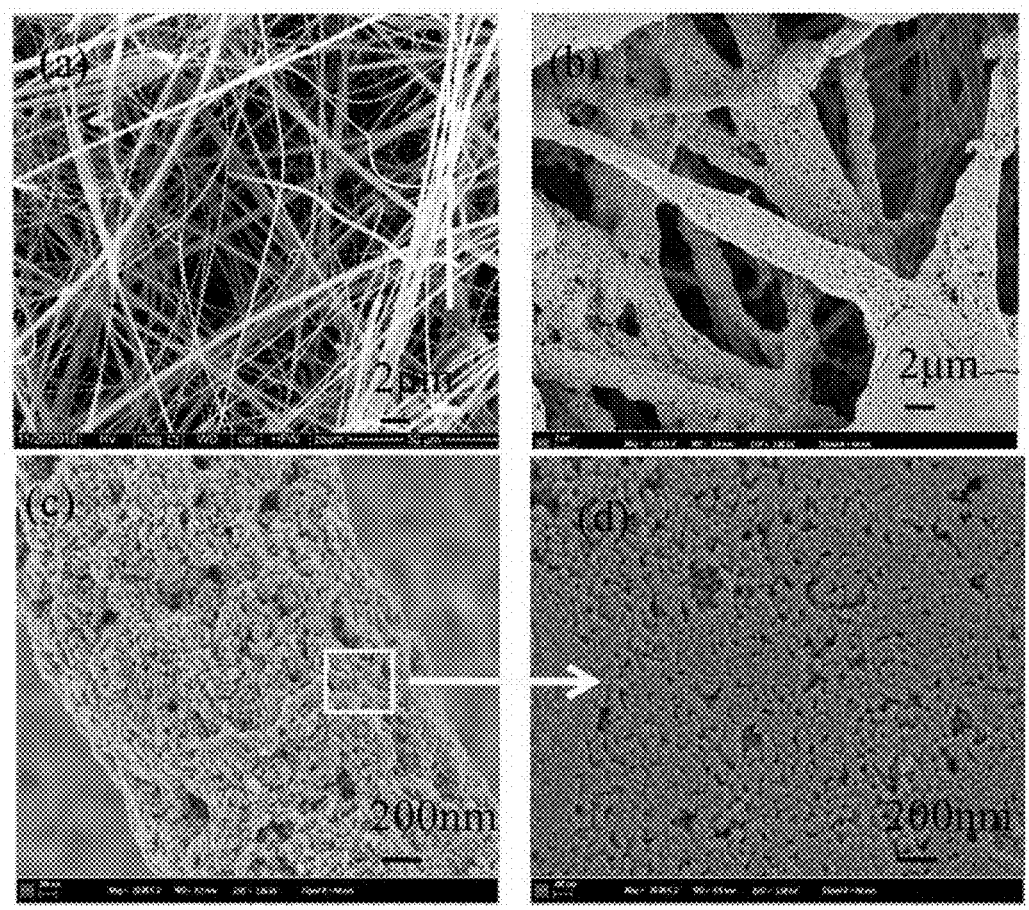
FIG. 2 is a scanning electron microscopy image of a glass fiber filter element according to an embodiment of the present disclosure.

FIG. 1 shows a schematic diagram of the glass fiber filter element of the present disclosure. As shown in FIG. 1, the superfine fibers with different diameters used in the present disclosure are mutually interlaced, crossed and overlapped. The filter element has a three-dimensional network porous structure and the nano-scale materials are loaded on the glass fibers. FIG. 2 shows a SEM image of the glass fiber filter element of the present disclosure. It can be seen from FIG. 2 that the nano-scale materials have a relatively small size and are densely and uniformly distributed on the glass fibers.

For the glass fiber filter element and the preparation method thereof provided in the present disclosure, the ultrafine glass fiber mat can be used to improve the air filtration performance. The nanoparticles such as zinc oxide and graphene oxide are introduced by the in-situ growth. This allows the filter element to photocatalytically degrade harmful substances in the air under the visible light, and improves the service life of the filter element at the same time. The preparation method of the filter element is relatively simple and has a low cost, which is suitable for the large-scale industrial production.

Example 1

40 parts of a glass fiber mat with a fiber diameter of 3.0 μm and 10 parts of a glass fiber mat with a fiber diameter of 1.0 μm were placed in an aqueous solution containing zinc oxide nanoparticles (prepared by the sol-gel method) and silver nanowires having a diameter of 20 nm for 5 min. A fiber dissociator stirred the solution at 6000 rpm to break the glass fiber mats and uniformly distribute glass fibers for 3 min, thereby obtaining a slurry with a concentration of 6 wt %. The slurry was transported to a paper machine by a slurry conveyor, and was wet-formed and made into a sheet. The formed wet sheet was immersed into an adhesive system including a polyurethane-modified phenolic resin and a silane coupling agent KH550 (a diluted solution with a concentration of 10 wt %). After this, the sheet was lifted, and dried on a drying plate at 100° C. for 5 min to obtain a filter paper. The filter paper was cut into a 4×4 cm spare.

2 g of zinc acetate was weighted and dissolved in 50 ml of deionized water, and added with 1.5 ml of ammonia. After precipitation, filtration was performed to obtain a zinc-ammonia complex and the zinc-ammonia complex was dried at 45° C. for 10 h. 3.4 g of the zinc-ammonia complex was weighted and used to prepare 0.85 mol/L zinc oxide precursor solution, of which 20 ml of ammonia and 20 ml of deionized water were used. 4 g of glucose was dissolved in 160 ml of deionized water, and was heated in a water bath at 50° C. for 4 h to obtain a mixture. The mixture was put into a Teflon reaction kettle, and the reaction kettle was placed in a constant temperature blast drying oven at 160° C. for 10 h, followed by standing for settlement overnight. 5 ml of a supernatant was taken and stirred fully.

The filter paper prepared above was immersed in a mixed solution of the zinc oxide precursor solution and the supernatant for 5 min, and lifted up at a speed of 1 cm/min, and then placed on a drying plate at 100° C. for drying. This immersing and drying process was repeated 4 times. The sample sheet was placed in $H_2$ atmosphere at 400° C. for 2 h and cooled, thereby obtaining a glass fiber filter paper. The prepared glass fiber filter paper was folded in a zigzag shape by a folding machine to form a glass fiber filter element for visible light photocatalysis and air purification.

50 ml of 10 mg/L Rhodamine B solution is degraded by the prepared glass fiber filter element under a visible light condition for 2 h. The prepared glass fiber filter element has a degradation efficiency of 85%. Moreover, the glass fiber filter element has a filtration resistance of 480 Pa, a filtration efficiency of 99.999%, and a strength of 0.9 KN/m.

Example 2

30 parts of a glass fiber mat with a fiber diameter of 3.5 μm, 10 parts of a glass fiber mat with a fiber diameter of 1.5 μm and 10 parts of a glass fiber mat with a fiber diameter of 0.5 μm were placed in an aqueous solution containing zinc oxide nanoparticles (prepared by the sol-gel method) and silver nanowires having a diameter of 15 nm for 6 min. A fiber dissociator stirred the solution at 8000 rpm to break the glass fiber mats and uniformly distribute glass fibers for 3 min, thereby obtaining a slurry with a concentration of 8 wt %. The slurry was transported to a paper machine by a slurry conveyor, and was wet-formed and made into a sheet. The formed wet sheet was immersed into an adhesive system including a polyurethane-modified phenolic resin and a silane coupling agent KH792 (a diluted solution with a concentration of 8 wt %). After this, the sheet was lifted, and dried on a drying plate at 110° C. for 5 min to obtain a filter paper. The filter paper was cut into a 4×4 cm spare.

4 g of zinc acetate was weighted and dissolved in 80 ml of deionized water, and added with 3 ml of ammonia. After precipitation, filtration was performed to obtain a zinc-ammonia complex and the zinc-ammonia complex was dried at 40° C. for 10 h. 6.8 g of the zinc-ammonia complex was weighted and used to prepare 1.7 mol/L zinc oxide precursor solution, of which 20 ml of ammonia and 20 ml of deionized water were used. 4 g of glucose was dissolved in 160 ml of deionized water, and was heated in a water bath at 60° C. for 6 h to obtain a mixture. The mixture was put into a Teflon reaction kettle, and the reaction kettle was placed in a constant temperature blast drying oven at 180° C. for 12 h, followed by standing for settlement overnight. 10 ml of a supernatant was taken and stirred fully.

The filter paper prepared above was immersed in a mixed solution of the zinc oxide precursor solution and the supernatant for 4 min, and lifted up at a speed of 1.5 cm/min, and then placed on a drying plate at 100° C. for drying. This immersing and drying process was repeated 5 times. The sample sheet was placed in $H_2$ atmosphere at 350° C. for 3 h and cooled, thereby obtaining a glass fiber filter paper. The prepared glass fiber filter paper was folded in a zigzag shape by a folding machine to form a glass fiber filter element for visible light photocatalysis and air purification.

50 ml of 10 mg/L Rhodamine B solution is degraded by the prepared glass fiber filter element under a visible light condition for 2 h. The prepared glass fiber filter element has a degradation efficiency of 80%. Moreover, the glass fiber filter element has a filtration resistance of 475 Pa, a filtration efficiency of 99.9995%, and a strength of 1.0 KN/m.

Comparative Example

The glass fiber mats were the same as those in Example 1 and processed in the same way as Example 1 except that no nanoparticles and nanowires were used.

Table 1 shows specific surface areas of the glass fiber filter elements prepared in Examples 1 and 2 and Comparative Example

| Sample | Example 1 | Example 2 | Comparative Example |
|---|---|---|---|
| specific surface area ($m^2/g$) | 2.3641 | 9.1035 | 11.4150 |

Figure 3:
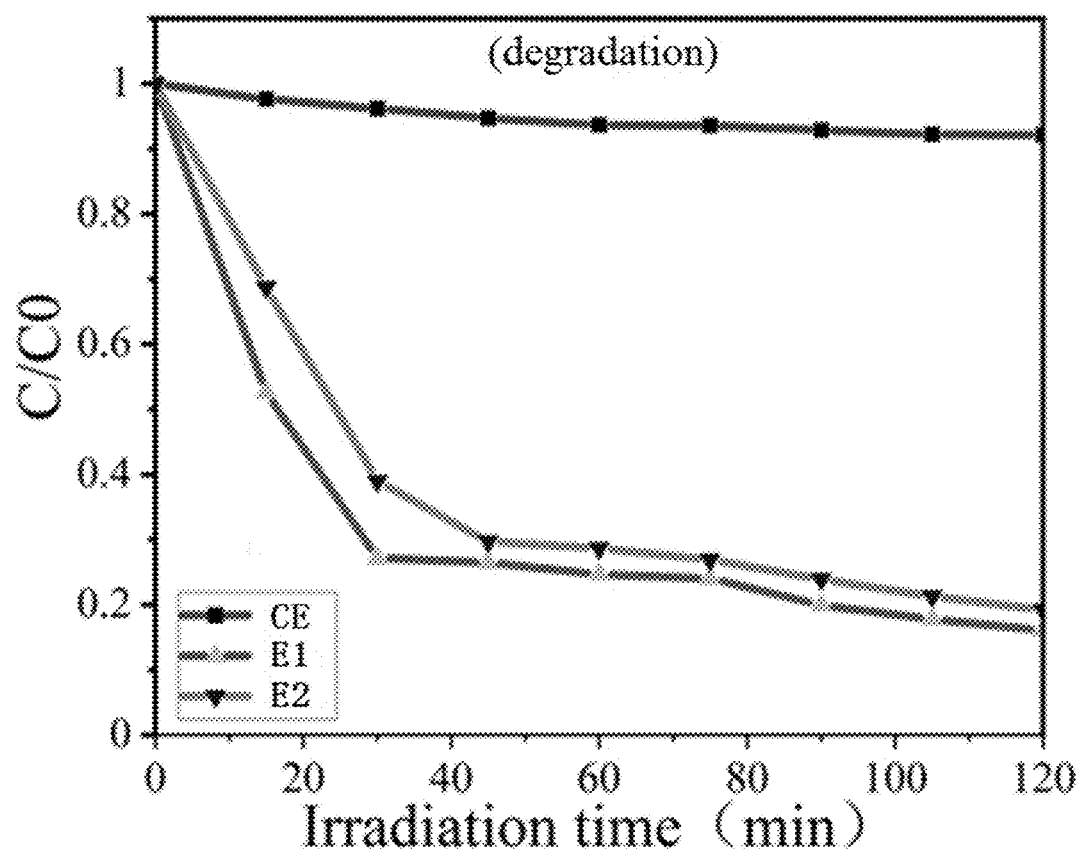
FIG. 3 is a graph showing degradation efficiencies of glass fiber filter elements of Examples 1 and 2 and Comparative Example of the present disclosure.

In addition, FIG. 3 shows degradation efficiencies of the glass fiber filter elements of Examples 1 and 2 and Comparative Example of the present disclosure. As shown in FIG. 3, the filter element prepared in Comparative Example has a degradation efficiency of approximate 9% (tested with 50 ml of 10 mg/L Rhodamine B solution), which is far below the degradation efficiencies achieved in Example 1 (85%) and Example 2 (80%).

In addition, terms such as "first" and "second" are used herein for purposes of description and are not intended to indicate or imply relative importance or significance or to imply the number of indicated technical features. Thus, the feature defined with "first" and "second" may include one or more of this feature.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from scope of the present disclosure.

What is claimed is:

1. A glass fiber filter element for visible light photocatalysis and air purification, comprising:
   4 to 7 wt % of nanoparticles comprising at least one selected from zinc oxide, graphene oxide, titanium oxide, and reduced graphene oxide,
   2 to 7 wt % of silver nanowires,
   3 to 12 wt % of an adhesive system, and
   78 to 91 wt % of a glass fiber mat,
   based on a total weight of the glass fiber filter element,
   wherein the glass fiber mat is made of at least two glass fibers with different diameters, and the diameters are in a range of 0.15 to 3.5 μm, the nanoparticles have a particle size from 1 to 200 nm, and the silver nanowires have a diameter of 15 to 50 nm, and
   wherein the glass fiber mat has a three-dimensional network porous structure, and the glass fibers with different diameters are mutually interlaced.

2. The glass fiber filter element according to claim 1, wherein the glass fiber mat comprises: 2.5 to 7.5 wt % of $Al_2O_3$, 4.5 to 8.5 wt % of MgO, 1.5 to 4.5 wt % of CaO, 3 to 6.5 wt % of $B_2O_3$, 4.5 to 7.5 wt % of a mixture of $Fe_2O$, ZnO and BaO, 8 to 10.5 wt % of an alkali metal oxide $R_2O$ where $R_2O$ is selected from $Na_2O$, $K_2O$ and a combination thereof, 56.5 to 66.5 wt % of $SiO_2$, based on the total weight of the glass fiber mat.

3. The glass fiber filter element according to claim 1, wherein the glass fiber mat is a matrix, and the nanoparticles and the silver nanowires are introduced by formation of a seed layer and in-situ growth.

4. The glass fiber filter element according to claim 1, wherein the adhesive system comprises an adhesive and a modifier.

5. The glass fiber filter element according to claim 4, wherein the adhesive is at least one selected from a pure acrylic emulsion, a silicone acrylic emulsion, a styrene acrylic emulsion, a vinegar acrylic emulsion and a modified phenolic resin, and
   wherein an amount of the adhesive is in a range of 2 to 5 wt % of the total weight of the glass fiber filter element.

6. The glass fiber filter element according to claim 5, wherein the modified phenolic resin is selected from a urea-modified phenolic resin, a polyurethane-modified phenolic resin and a melamine-modified phenolic resin.

7. The glass fiber filter element according to claim 4, wherein the modifier is a silane coupling agent, and an amount of the modifier is in a range of 1 to 3 wt % of the total weight of the glass fiber filter element.

8. The glass fiber filter element according to claim 1, wherein a zinc source for providing zinc oxide of the nanoparticles is at least one selected from zinc nitrate hexahydrate, zinc acetate, zinc sulfate, and zinc carbonate.

9. The glass fiber filter element according to claim 1, wherein a titanium source for providing titanium oxide of the nanoparticles is at least one selected from tetrabutyl titanate, titanium tetrachloride, and titanium alkoxide.

10. The glass fiber filter element according to claim 1, wherein the nanoparticles have a particle size from 1 to 10 nm.

11. A method for preparing the glass fiber filter element for visible light photocatalysis and air purification according to claim 1, comprising:
   (1) selecting two or more glass fiber mats with different glass fiber diameters, putting the glass fiber mats into a mixed liquid containing nanoparticles and silver nanowires, and using a fiber dissociator for stirring the mixed liquid to obtain a slurry;
   (2) transporting the slurry to a paper machine for wet forming to obtain a wet paper with a seed layer of the nanoparticles, immersing the wet paper in an adhesive system, and drying the wet paper to obtain a glass fiber paper;
   (3) immersing the glass fiber paper in a solution comprising the nanoparticles or precursors thereof, and drying the glass fiber paper;
   (4) performing an annealing process on the glass fiber paper to obtain a filter paper; and
   (5) folding the filter paper in a zigzag shape to obtain the glass fiber filter element.

12. The method according to claim 11, wherein the glass fiber mat has glass fibers with a diameter of 0.15 to 3.5 μm.

13. The method according to claim 11, wherein two glass fiber mats are used, and one of the glass fiber mats has a glass fiber diameter of 3.0 μm and the other one of the glass fiber mats has a glass fiber diameter of 1.0 μm.

14. The method according to claim 11, wherein in step (1), the fiber dissociator has a revolving speed of 5000 to 12000 rpm, and the slurry has a concentration of 5 to 10 wt % and a pH value of 3.0 to 5.0.

15. The method according to claim 11, wherein the drying in step (2) is baking on a drying plate at a temperature of 100 to 115° C. for 5±1 min.

16. The method according to claim 11, wherein the solution in step (3) comprises a zinc oxide precursor solution, and the zinc oxide precursor solution is prepared by:
   dissolving zinc acetate in deionized water, adding ammonia to obtain a precipitate, filtering the precipitate and drying the precipitate, and preparing the zinc oxide precursor solution having a molar concentration of 0.5 to 3.0 mol/L with the precipitate, ammonia and deionized water.

17. The method according to claim 11, wherein the solution in step (3) comprises a graphene oxide solution, and the graphene oxide solution is prepared by:
   dissolving glucose in deionized water to obtain an aqueous solution, heating the aqueous solution in a water bath at a temperature of 40 to 60° C. for 6 to 8 h, putting the aqueous solution in a Teflon reaction kettle, and placing the reaction kettle in a constant temperature blast drying oven at a temperature of 160 to 200° C. for 10 to 12 h, followed by standing for settlement and taking a supernatant as the graphene oxide solution.

18. The method according to claim 11, wherein during the immersing in the step (2), the wet paper is lifted up at a lifting speed in a range of 0.5 to 5 cm/min.

19. The method according to claim 11, wherein the annealing process in the step (4) is performed in an $H_2$ atmosphere at a temperature of 100° C. to 400° C. for 1 to 4 h.

* * * * *